United States Patent [19]
Roach et al.

[11] 4,357,603
[45] Nov. 2, 1982

[54] METHOD AND APPARATUS FOR ACOUSTICALLY MONITORING THE FLOW OF SUSPENDED SOLID PARTICULATE MATTER

[75] Inventors: Paul D. Roach, Darien; Apostolos C. Raptis, Downers Grove, both of Ill.

[73] Assignee: The United States of America as represented by the Depart of Energy, Washington, D.C.

[21] Appl. No.: 209,928

[22] Filed: Nov. 24, 1980

[51] Int. Cl.³ .............................................. G08B 21/00
[52] U.S. Cl. ................................. 340/627; 340/608; 73/861.21
[58] Field of Search ............... 340/606, 607, 608, 627; 73/861.04, 861.18, 861.25, 861.04, 61 R

[56] References Cited

U.S. PATENT DOCUMENTS

| | | | |
|---|---|---|---|
| 2,659,881 | 11/1953 | Bogot et al. | 340/608 |
| 2,760,184 | 8/1956 | Beattie | 340/606 |
| 2,936,619 | 5/1960 | Gibney | 73/194 |
| 3,068,694 | 12/1962 | Worswick | 73/194 |
| 3,343,126 | 9/1967 | Corda | 340/627 |
| 3,434,335 | 3/1969 | Langer | 340/627 |
| 3,580,092 | 5/1971 | Scarpa | 73/194 |
| 3,710,615 | 1/1973 | Johnson et al. | 340/627 |
| 3,816,773 | 6/1974 | Baldwin et al. | 73/861.04 |
| 4,112,740 | 9/1978 | Brandestini | 340/608 |
| 4,152,928 | 5/1979 | Roberts | 73/861.25 |

*Primary Examiner*—Gerald L. Brigance

[57] ABSTRACT

A method and apparatus for monitoring char flow in a coal gasifier system includes flow monitor circuits which measure acoustic attenuation caused by the presence of char in a char line and provide a char flow/no flow indication and an indication of relative char density. The flow monitor circuits compute the ratio of signals in two frequency bands, a first frequency band representative of background noise, and a second higher frequency band in which background noise is attenuated by the presence of char. Since the second frequency band contains higher frequencies, the ratio can be used to provide a flow/no flow indication. The second band can also be selected so that attenuation is monotonically related to particle concentration, providing a quantitative measure of char concentration.

6 Claims, 9 Drawing Figures

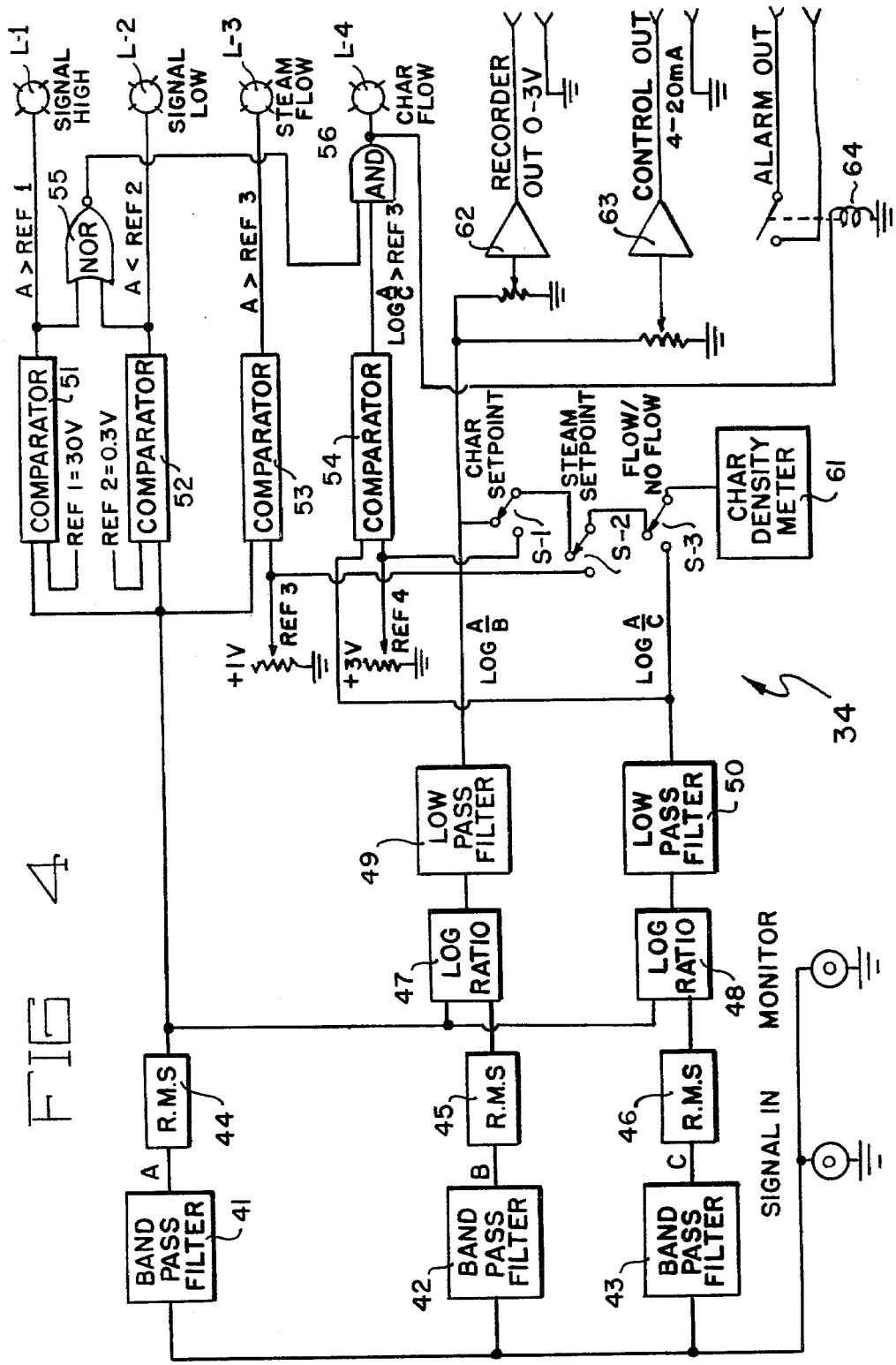

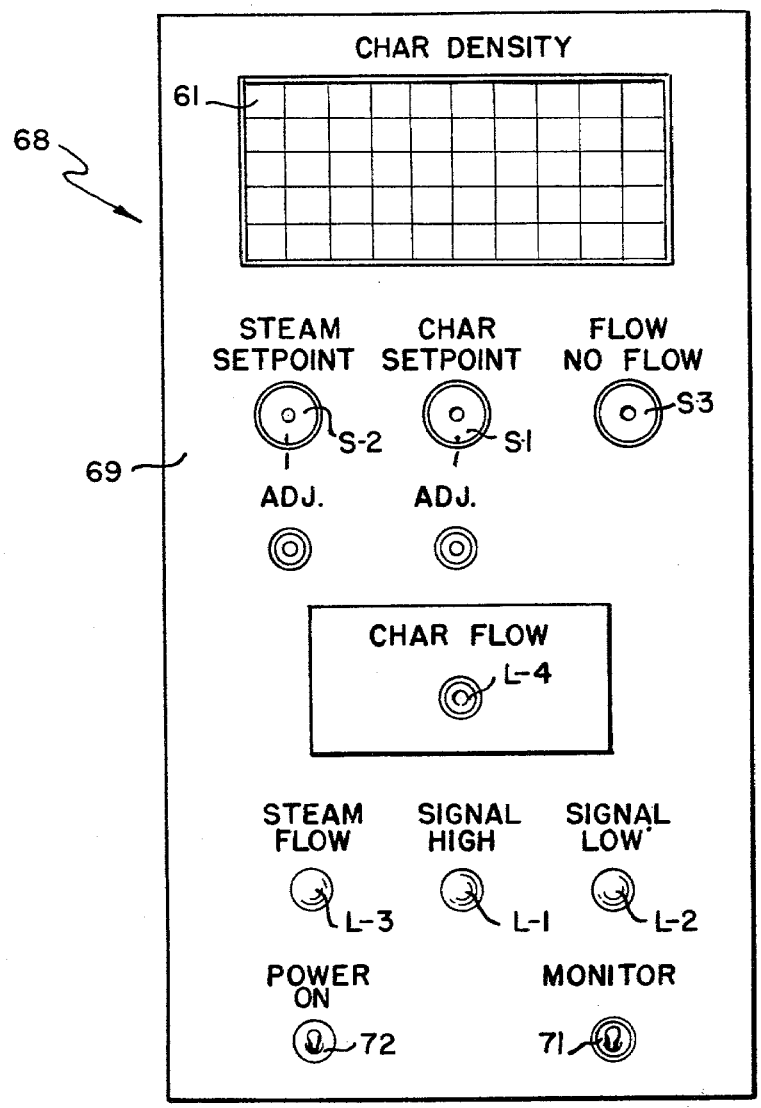

METHOD AND APPARATUS FOR ACOUSTICALLY MONITORING THE FLOW OF SUSPENDED SOLID PARTICULATE MATTER

CONTRACTUAL ORIGIN OF THE INVENTION

The United States Government has rights in this invention pursuant to Contract No. W-31-109-Eng-38 between the U.S. Department of Energy and Argonne National Laboratory.

BACKGROUND OF THE INVENTION

This invention relates generally to a method and apparatus for acoustically monitoring the flow of suspended solid particulate matter; and specifically to a method and apparatus for measuring such flow under high temperatures and pressures in multiphase process streams. The invention has particular application in coal gasification processes and the monitoring char flow.

In the process of converting coal into liquid fuels or high and low Btu gases, problems with the flow of particulate matter are most frequently encountered with char, a solid residue that remains after the removal of moisture and volatile matter from coal. Blockage of char feed lines has been a recurrent problem that can lead to serious interruption of the coal conversion process and create serious safety hazards.

Char particles are abrasive and also tend to plug up orifices and to foul up moving parts. Typical operating conditions within the char feed lines in coal gasification processes are 430° C. (800° F.) at a pressure of 11.4 MPa (1650 psi).

SUMMARY OF THE INVENTION

The present invention provides for a method and apparatus for acoustically monitoring the flow of solid particulate matter through pipes. An embodiment of the present invention features a relatively streamlined geometry, minimizing flow obstruction and instrument erosion; thus, allowing its use in a highly erosive environment of flowing particulate matter.

The present invention has the further advantage of being able to operate at high temperatures. An embodiment of the invention includes a high temperature microphone able to withstand temperatures up to 650° C. (1200° F.) and pressures up to 14 MPa (2000 psi).

The present invention, when used in char lines in a coal conversion processing system, requires little modification of present procedures or of the physical plant.

Briefly, the invention includes acoustic monitors which give rapid indication of blockages or other flow perturbations in conduits carrying particulate matter. These monitors use a microphone for measuring the acoustic attenuation caused by the presence of the particulate matter in the line. Such a measurement gives a sensitive indication of the solid particulate matter flowing in the line that can be used for both process control and rapid detection of blockages.

In the present invention, a localized noise source, such as a steam eductor, provides a background noise within the conduit. When solid particulate matter is present in the stream, we have found out that the attenuation characteristic is frequency dependent in such a manner that for low frequencies, the attenuation is little or none, for higher frequencies, the attenuation increases monotonically as particle concentration increases, and that for still higher frequencies, the attenuation is most pronounced. The present invention determines acoustical energy in a first or low frequency band representative of background noise, and in a second or higher frequency band in which the background noise is attenuated by the presence of solid particulate matter. The invention includes means for computing the ratio of the signals in the two frequency bands. If the second frequency band contains measurable acoustical energy, the ratio can be used as an indication of flow or no flow conditions. The second frequency band can also be selected such that the amount of attenuation is monotonically related to the concentration of particles, in which case the ratio, after calibration, may be used as a quantitative measure of concentration of solid particles in the stream.

Other features and advantages of the present invention will be apparent from the following description and claims and are illustrated in the accompanying drawings.

DESCRIPTION OF THE DRAWINGS

FIG. 4 is a block diagram of the flow monitor circuits provided by the present invention;

FIG. 5 is a plan view of a char flow monitoring module illustrating its control panel.

DESCRIPTION OF THE PREFERRED EMBODIMENT

The present invention is particularly suited for use in the coal conversion field where flow monitors are needed that can handle the multiphase process streams. These streams are frequently operated at high pressures and temperatures and are very erosive. Available flow meters are usually not able to withstand such a hostile environment. Of particular concern, is monitoring the flow of char, a solid particulate residue that remains after the removal of moisture and volatile matter from powdered coal. One example of a char feed line operates at a temperature of 430° C. (800° F.) and a pressure of 11.4 MPa (1,650 psi). The present invention will be described in detail as it applies to the monitoring of char flow in the above mentioned char feed line, or coal conversion process.

Figure 1:
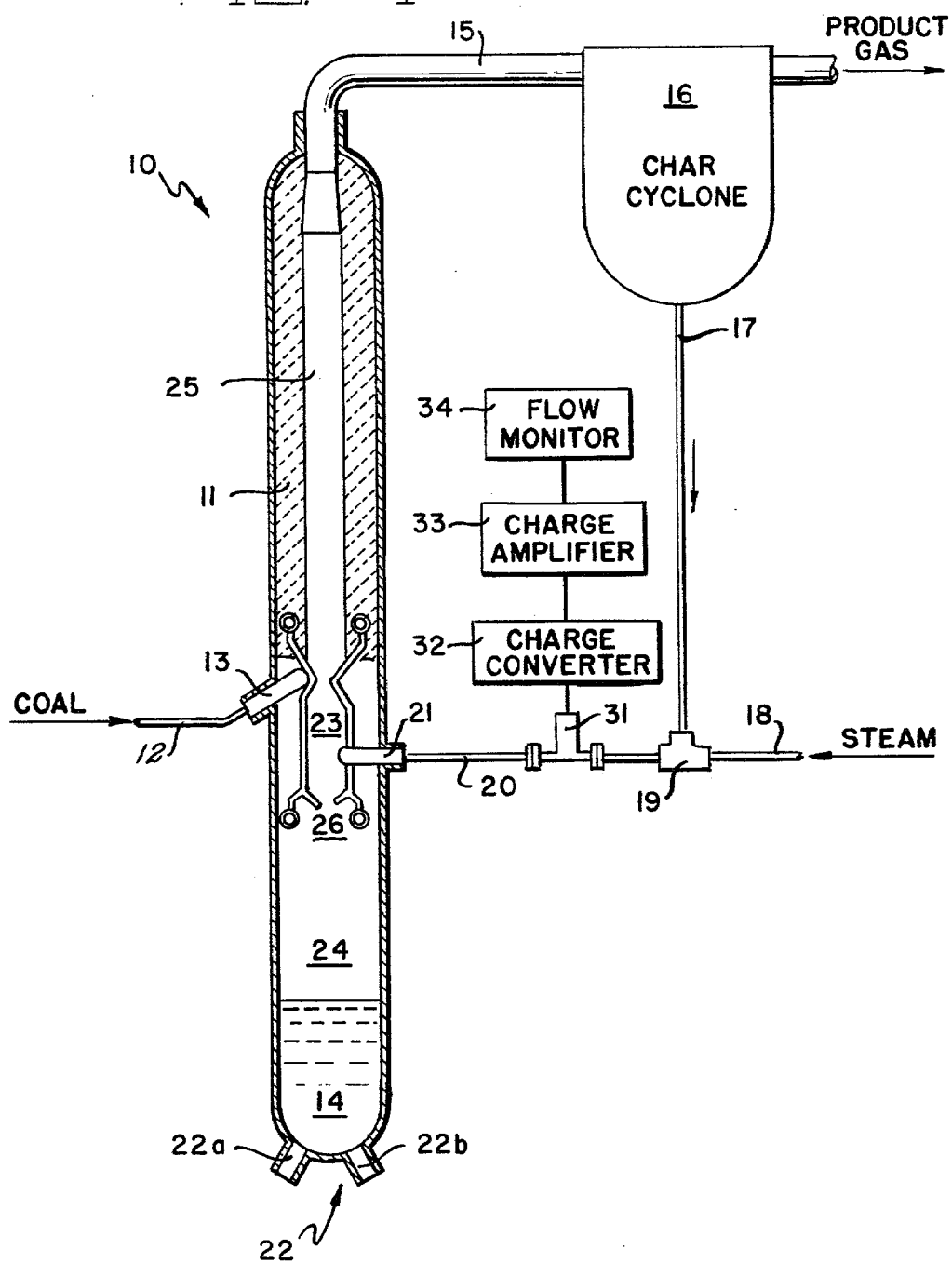
FIG. 1 is a schematic diagram of a two stage high pressure coal gasification apparatus employing the char flow monitoring apparatus of the present invention in one of the char lines thereof.

A coal gasification apparatus or gasifier 10, involving two stage high pressure coal gasification in an entrained bed type of reactor vessel 24, is shown schematically in FIG. 1. The coal gasification apparatus 10 includes a reactor vessel 24 having an upper 25 and lower 26 stage. The upper stage 25 includes a refractory wall 11 for retaining heat within the vessel 24. Powdered coal is fed to the upper stage 24 by means of two coal feed lines 12 (of which only one is shown) and two coal injection nozzels 13 (of which only one is shown). The powered coal is swept upward by rising hot gases from the lower stage into a balanced suspension of small solid particles. In the upper stage 24, the powdered coal is devolatilized and partly gasified as it contracts the hot gases rising from the lower stage.

The gases and the residual char travel up the reactor vessel 24 and through an exit pipe 15 to a char cyclone 16. The gases and char are separated in the char cyclone 16. After passing through the char cyclone 16, the gases go to a shift reactor (not shown) and a fluidized bed methanator (not shown) to produce pipeline gas.

The char drops approximately 16 meters by gravity feed from the cyclone 16 through three vertical char lines 17 (of which only one is shown) to three steam eductors 19 (of which only one is shown). High pressure steam from the steam line 18 is added to the char at each of the steam eductors 19. The char and steam then move horizontally a distance of three meters through three horizontal char lines 20 (only one of which is shown) to the nozzles of three char burners 21 (of which only one is shown).

The char and steam are fed into a reaction chamber 23 located in the lower stage 26 of the vessel 24. In the lower stage 26, the char reacts with steam and oxygen under much hotter conditions (1370°–1650° C., 2500°–3000° F.) producing a mixture of gases that is rich in hydrogen. The waste or slag, is molten at this temperature and flows to the water cooled quench zone 14, while the hot gases rise to the upper stage 25 of the reactor vessel 24 sweeping powdered coal upward from the coal injection nozzles 13 completing a cycle.

Blockage of the char feed lines 17 and 20 between the char cyclone 16 and the char burners 21 has been a recurrent problem. Blockage of the char in either the vertical 17 or horizontal 20 lines can cause a very serious interruption of the gasification operation and quickly lead to a hazardous temperature excursion in the gasifier 10, in addition to causing steam to travel up into the char cyclone 16.

It has been found that the steam eductor is an advantageous source of acoustic noise. A microphone 31 positioned in the horizontal char line produces a strong, broad-band background noise signal associated with the steam flow. The presence of char particles causes absorption and scattering of the acoustic energy generated by the steam eductor, resulting in a detectable decrease in the background noise signal. The monitoring apparatus, which includes the microphone 31, a charge converter 32, a charge amplifier 33 and a flow monitor circuit 34, measures the acoustic attenuation caused by the presence of char in the char line and provides a char flow/no flow indication, and an indication of relative char density or flow.

A spectral analysis of the microphone signal is shown in FIGS. 2A–2D for various rates of char flow. The microphone signal was analyzed using a Type SD 301 Real Time Analyzer, and a Type SD 309 Ensemble Averager, and displaying the results on an oscilloscope. In each figure, the upper trace is the spectrum of the signal when only steam is flowing in the char line. The lower trace is the spectrum taken when char is also flowing. Although the exact amount of char cannot be determined using the microphone signal alone, the relative flow rate of the char can by inferred from valve openings and readings of differential pressure instruments.

Figure 2A:
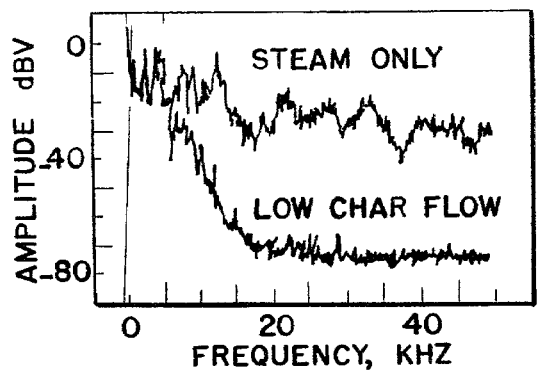
FIGS. 2A–2D illustrate the spectrum analysis of the signal output of a microphone of the char flow monitoring apparatus under different char flow conditions.
Figure 2B:
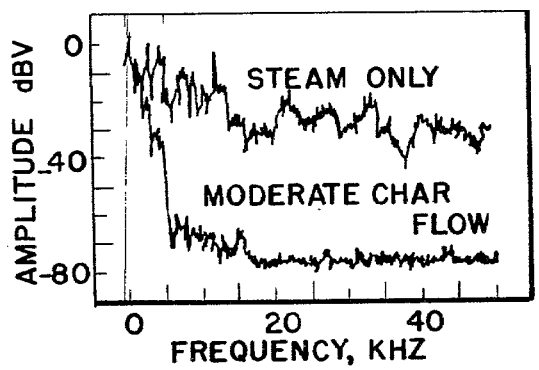
Figure 2C:
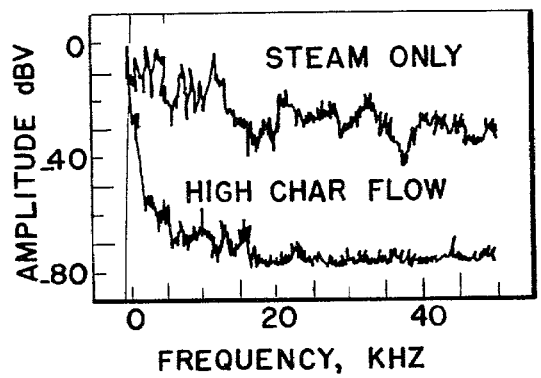
Figure 2D:
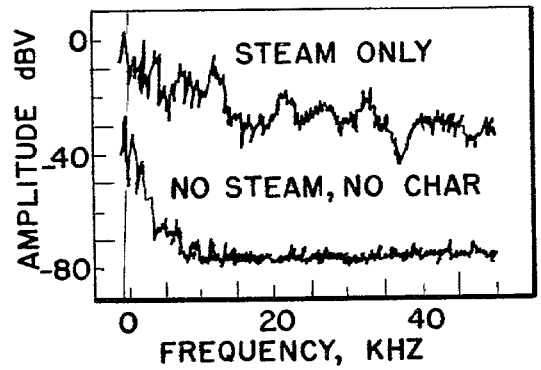

FIGS. 2A, 2B and 2C illustrate the microphone output signal provided for low, moderate and high relative char flow rates, respectively. The lower trace in FIG. 2D shows the spectrum with no char and no steam flowing. All the spectra shown in FIGS. 2A–2D were taken with analysis bandwidth of 300 Hz. The reference level at 0 dB corresponds to 1.0 v RMS at the output of the remote charge converter 32 (FIG. 1).

The spectrum of the "steam-only" signal (the upper traces in FIGS. 2A–2D) clearly shows that the acoustic signal background (noise) from the steam eductor is quite strong and rather uniformly distributed over a frequency range of 0–50 kHz. It is apparent from FIGS. 2A–2C that the signal attenuation increases with both frequency and char concentration.

In a low band of frequencies of the microphone output signal, ranging from 200 Hz to 1 kHz, there is little or no attenuation. In an intermediate band of frequencies of the microphone output signal, ranging from 1 kHz to 5 kHz, attenuation increases monotonically with particle concentration. In a high band of frequencies of the microphone output signal, ranging from 20 kHz to 50 kHz, attenuation is most pronounced.

The flow monitor circuit 34 computes ratios of the signals in the above-mentioned frequency bands. The low frequency band (200 Hz to 1 kHz) is representative of background noise. Signals in the intermediate and high frequency bands are normalized to the signal in the low frequency band. In the intermediate frequency band (1 kHz–5 kHz), the amount of attenuation is monotonically related to the concentration of particles in the char line. The ratio of the signal in the intermediate frequency band to the signal in the low frequency band is used as a measure of char concentration. This measure, after calibration, will provide a quantitative measure of char concentration. The ratio of the signal in the high frequency band to the signal in the low frequency band provides a char flow/no flow indication.

Figure 3:
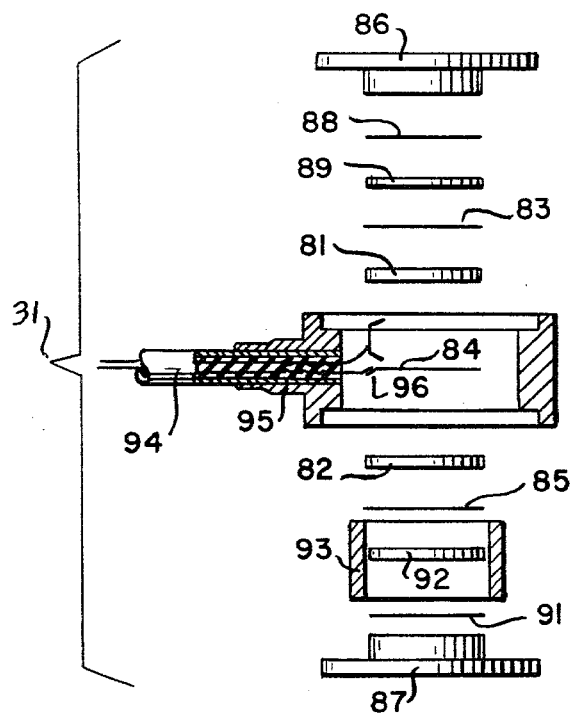
FIG. 3 is an exploded view of a high temperature microphone of the char flow monitoring apparatus.

Referring to FIG. 3, the microphone 31 includes a section comprised of two lithium niobate piezoelectric discs 81 and 82 which are sandwiched between three platinum foil electrodes 83, 84 and 85. Upper and lower diaphragms 86 and 87 transmit to discs 81, 82 forces due to acoustic signals associated with the flow of steam and char. A platinum foil cushion 88 and a sapphire insulating disc 89 separate the upper diaphragm 86 from the upper electrode 83 of the transducer section. Similarly, a further platinum foil cushion 91 and sapphire insulating disc 92 separate diaphragm 87 from the lower electrode 85. The discs 81, 82, 89 and 92, the electrodes 83–85 and the cushions 88 and 91 are maintained in alignment by an alumina alignment ring 93 which in turn is positioned within a body ring 94, which serves as a housing for the microphone. The signal connection is by means of a metal sheathed two-conductor cable 94 which passed through connection member 95.

The two discs of lithium niobate of the transducer assembly are arranged back-to-back with respect to their piezoelectric polarities. This makes the microphone sensitive to pressure changes on the faces of the discs, but it is relatively insensitive to vibration of the device as a whole. Accordingly, the microphone must by immersed in the flow.

As illustrated in FIG. 1, the microphone is installed in the horizontal section of the char feed line. A hole (not shown) in the wall of the char line allows one end of the microphone to be inserted into the line with its lower edge flush with the inner surface of the char line. This permits the microphone to sense pressure fluctuations in the process stream with minimal disturbance to the flow and negligible erosion of the microphone.

The microphone may be installed in the char line by any suitable mechanical means which provides the necessary high temperatures high pressure seal. For example, a two-inch tee section may be connected in series with the char line using Grayloc fittings. The microphone may be supported by a Grayloc hub with mates with a matching hub welded to the branch of the tee section.

The charge converter 32, Endevco Model 2732A, converts the charge signal from the microphone 31 to a low-impedance voltage signal suitable for transmission over long lengths of cable. The charge to voltage conversion ratio is 3.3 mV/pC. The charge converter is located near the microphone. Power to activate the converter circuits is supplied through the output signal cable which is connected to the charge amplifier 33.

The charge amplifier 33, Endevco Model 2735, provides variable amplification of the voltage from the charge converter 32, and provides the DC power required by the charge converter. Voltage gains for the charge amplifier vary from 0.09 to 270 in eight steps. Combined with the charge conversion ratio of the charge converter, this provides a sensitivity which varies from 0.30 to 900 mV/pC.

Referring to FIG. 4, the flow monitor circuit 34, shown in block diagram form, processes the microphone signal and provides both the flow/no flow indication and the char density indication.

Briefly, the flow monitor circuit 34 includes three band-pass filters 41–43 which divide the microphone output signal into three frequency bands: 200 Hz to 1 kHz, 1 kHz to 5 kHz and 20 kHz to 50 kHz. This provides three signal components: signal A (low frequency band), signal B (intermediate frequency band) and signal C (high frequency bands). Three RMS detectors 44-46 and two log ratio converters 47, 48 generate a DC voltage proportional to the log of the ratios of the signal amplitudes in these frequency bands. The RMS detectors 44-46 provide a DC output proportional to the signal in the corresponding band. The converters 44-46 comprise the commercially available Type AD 442J. The log ratio converters 47, 48 comprise commercially available type AD 757N. Low pass filter circuits 49 and 50 reduce jitter and provide adjustable time constants for the normalized signals. Since signal A (the lowest frequency component) is least attenuated by the char, it therefore provides a measure of the previously mentioned "steam-only" signal. This signal is taken as the amplitude reference. The other signals B and C are normalized to this reference by the log ratio circuits 47, 48, respectively.

The intermediate frequency signal B provides a usable signal over a wide range of char density. The log ratio circuit 47 takes the logarithm of signals A and B in the form of LOG A/B, providing a signal which is proportional to the amount of signal attenuation in the frequency range of 1 to 5 kHz, and corresponds to the amount of char flowing in the char line where the microphone 31 is located. The log ratio circuit 48 takes the logarithm of signals A and C in the form LOG A/C, providing a signal which is proportional to high frequency signal attenuation in the range of 20 kHz to 50 kHz. The log ratio circuit 48 also comprises the commercially available Type AD 757N. Signal B, when normalized to the reference signal A (i.e. LOG A/B), provides a char density signal which is supplied to a digital char density meter 61, providing a continuous indication of char density. The signal is also supplied to driver circuits 62, 63 which provide voltage and current outputs, respectively, for driving a recorder or process control system.

The high frequency signal C is most sensitive to the presence of char and this signal is used to generate the flow/no flow indication. The normalized signal (LOG A/C) is compared in comparator circuit 54 with a reference signal REF 4 representing a char setpoint to provide a flow/no flow signal. This signal is generated whenever the amplitude of the high frequency signal C is below a certain level relative to the low frequency signal A. Under these conditions, the flow/no flow lamp L4 is lit, indicating a char flow condition. The flow/no flow signal also operates an alarm relay 64 normally providing a contact closure under char flow conditions.

The low frequency signal A is compared with first and second reference voltage REF 1, REF 2 in respective comparator circuits 51 and 52, which provide outputs for lighting indicator lamps L1 or L2 whenever A signal amplitude is not within a desired range. A NOR gate 55, which has its inputs connected to the outputs of the comparator circuits 51 and 52, generates an inhibit signal whenever the reference signal A is out of range. This inhibit signal disables an AND gate 56 to prevent lighting of the flow/no-flow indicator L4. A further comparator circuit 53 compares signal A with a reference signal REF 3, representing a steam setpoint, and lights an indicator L3 whenever signal A exceeds this setpoint value. Switches S1, S2 and S3 enable the char setpoint, the steam setpoint, and the flow/no flow signal, respectively, to be displayed on the digital meter. The primary function of the digital meter is to display the value of the char density signal. As char density varies from zero to a maximum value, this signal will vary from about 1 to 2.5. This signal is always displayed unless one of the setpoint switches S1 and S2 or the flow/no-flow switch S3 is operated. In that case, the meter displays the corresponding signal.

Referring to FIG. 5, the flow monitor circuit is enclosed within a housing 68 which has a front panel 69 which mounts the digital meter 61, the setpoint switches S1-S3, and the four indicators L1-L4. The front panel also mounts a monitor connector 71 which enables external monitoring of the amplified microphone signal. A power indicator 72 is lit whenever the flow monitoring circuits are energized. The microphone input, the voltage and current outputs, and alarm relay output are provided at the back panel of the housing 68 and are not illustrated in FIG. 5.

A flow monitor test circuit (not shown) may be provided which generates different pseudo-noise signals for simulating microphone operation under different operating conditions to enable testing of the flow monitoring circuit to confirm proper operation of all of the flow monitor circuits.

Although only one flow monitor module is described, three identical modules are used with separate microphones, one for each of the three char legs.

Figure 6:
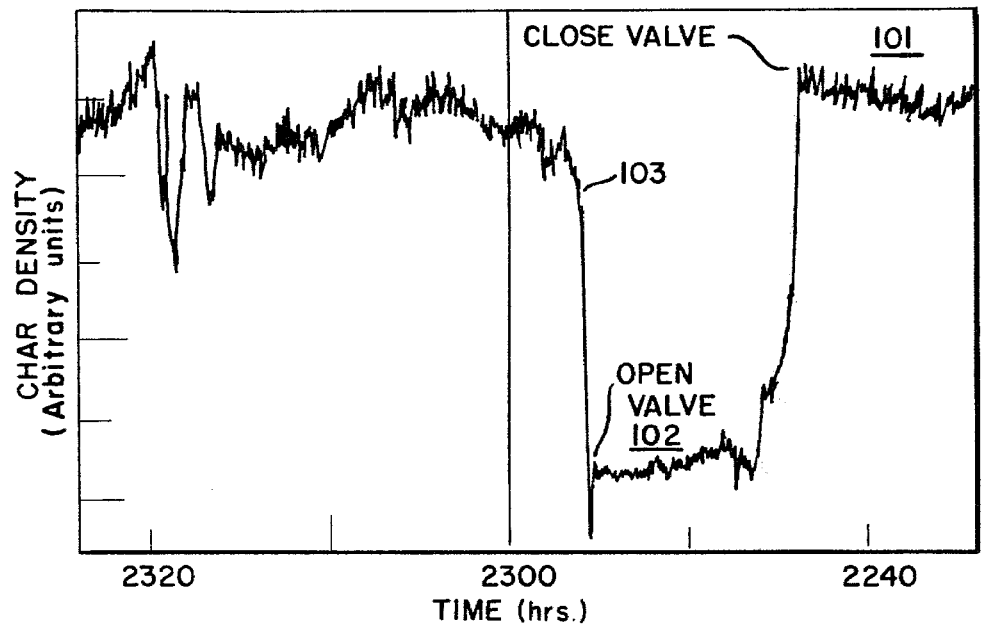
FIG. 6 is a representation of a recording of a char density signal illustrating a temporary interruption in char flow.

Referring to FIG. 6, there is shown an illustration of a recording of the char density signal for an operating cycle in which an interruption of char flow occurs. The char density signal is uncalibrated and is plotted in arbitrary units as a function of time, increasing from the right hand side of FIG. 6 towards the left hand side. Referring to FIG. 4, initially with char flowing, the log ratio circuit 47 responds to the low and intermediate frequency portions of the amplified microphone signal to provide a relatively high char density signal to recorder driver 62 as illustrated at 101 in the right hand portion of FIG. 6. Also, log ratio circuit 48 responds to the low and high frequency components of the microphone signal to enable comparator 54, since it is assumed the char setpoint is exceeded, to light the char flow indicator L4.

At 2245 hours, marked "close valve" on the record, a char flow blockage occurs in the horizontal leg of the char line, necessitating a shutdown of the char burner. The interruption in char flow causes the char flow signal generated by log ratio circuit 48 to fall below the char setpoint causing the char flow lamp L4 to be extinguished. Also, there is a significant decrease in the char density signal generated by log ratio circuit 48 as indicated at 102 in FIG. 6.

The extinguishing of the char flow lamp L4 and the drop in the char density signal alerts the operator that a blockage of char flow has occurred, so that the operator may take the steps necessary to alleviate the problem. For example, the operator may close a valve in the char leg forcing steam flow along the horizontal leg to the char line to dislodge the plug.

At 2256 hours, the char burner was relit and char flow resumed (marked "open valve" on the record). The char flow lamp L4 will again be lit and the char density signal increases to nearly its initial value as indicated at 103 in FIG. 6. As illustrated, char flow is somewhat less stable at this time since the char flow is initially unsteady following opening of the valve in the char leg.

The sensitivity and speed and response of the flow monitor apparatus is clearly illustrated in FIG. 6. Even though the char density signal is uncalibrated, it provides valuable information to the plant operator. Stability of the flow is easily judged, and the char density signal allows the operator to know when a previous flow rate has been achieved.

While the above describes solid particulate in a fluid flow, this invention pertains, in its broader sense, to the monitoring of a substance in a fluid, where the density of the substance differs from the density of the fluid flowing, such that acoustical energy transmitted through the flow is scattered or absorbed by the substance.

The embodiments of the invention in which an exclusive property or privilege is claimed are defined as follows:

1. An acoustic apparatus for monitoring the flow of particulate matter in a flowable medium, the flowable medium being characterized in having an acoustic noise distribution over a broad frequency spectrum, comprising:

a transducer coupled to said flowable medium to sense sound waves therein and to generate an electrical signal representative of the flow of the particulate matter in said flowable medium;

a filter circuit, coupled to said transducer, and comprising a low frequency band pass filter to generate a first output signal, an intermediate frequency band pass filter to generate a second output signal, and a high frequency band pass filter to generate a third output signal;

a first ratio circuit coupled to said low frequency band pass filter and said intermediate frequency band pass filter to generate a first ratio signal, said first ratio signal being a function of said first output signal divided by said second output signal and being representative of the relative concentration of the particulate matter in the flowable medium; and a second ratio circuit coupled to said low frequency band pass filter and said high frequency band pass filter to generate a second ratio signal, said second ratio signal being a function of said first output signal divided by said third output signal and being representative of the flow/no-flow condition of the particulate matter in the flowable medium.

2. The apparatus of claim 1 wherein said first and second ratio circuits include means for developing first and second log signals equal to the log of said first and second ratio signals, respectively, said first log signal being representative of the relative concentration of the particulate matter in the flowable medium and said second log signal being representative of the flow/no-flow condition of the particulate matter in the flowable medium.

3. The apparatus of claim 2 wherein said first output signal extends through the frequency band from 0.2 KHz to 1 KHz, said second output signal extends through the frequency band from 1 KHz to 5 KHz, and said third output signal extends through the frequency band from 20 KHz to 50 KHz.

4. The apparatus of claim 3 further comprising an alarm circuit coupled to said low frequency band pass filter and said second ratio circuit to generate an alarm signal in response to an unacceptable flow condition.

5. The apparatus of claim 3 wherein said flowable medium is steam and said particulate matter is char.

6. The apparatus of claim 3 further comprising a recorder coupled to said first ratio circuit to provide a measure of the relative concentration of particulate matter in the system.

* * * * *